(12) United States Patent
Dalton et al.

(10) Patent No.: US 11,337,640 B2
(45) Date of Patent: May 24, 2022

(54) MULTIFUNCTIONAL SMELL TEST

(71) Applicants: Monell Chemical Senses Center, Philadelphia, PA (US); Temple University—of The Commonwealth System of Higher Education, Philadelphia, PA (US)

(72) Inventors: Pamela H. Dalton, Philadelphia, PA (US); Danielle Reed, Glenside, PA (US); Valentina Parma, Philadelphia, PA (US); Maureen O'Leary, Narberth, PA (US); Mackenzie Hannum, Philadelphia, PA (US)

(73) Assignees: MONELL CHEMICAL SENSES CENTER, Philadelphia, PA (US); TEMPLE UNIVERSITY—OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 0 days.

(21) Appl. No.: 17/111,114

(22) Filed: Dec. 3, 2020

(65) Prior Publication Data

US 2022/0117541 A1 Apr. 21, 2022

Related U.S. Application Data

(60) Provisional application No. 63/092,983, filed on Oct. 16, 2020.

(51) Int. Cl.
*A61B 5/00* (2006.01)
*G16H 10/40* (2018.01)
*G16H 10/20* (2018.01)

(52) U.S. Cl.
CPC .......... *A61B 5/4011* (2013.01); *A61B 5/4082* (2013.01); *A61B 5/4088* (2013.01);
(Continued)

(58) Field of Classification Search
USPC ........................................................ 600/303
See application file for complete search history.

(56) References Cited

U.S. PATENT DOCUMENTS 6,132,830 A * 10/2000 O'Halloran ........ A45D 40/0087
428/320.2
6,558,322 B1 * 5/2003 Busch ................ G01N 33/0001
600/303

(Continued)

FOREIGN PATENT DOCUMENTS

EP 2174585 A1 * 4/2010 ........... A61B 5/4011

OTHER PUBLICATIONS

<https://www.hhgrfx.com/special-effects-screen-printing-uv-coating-applications/smell-test-printing/> (Year: 2021).*

(Continued)

*Primary Examiner* — Shirley X Jian
(74) *Attorney, Agent, or Firm* — Wilson Sonsini Goodrich & Rosati

(57) ABSTRACT

Provided are systems, methods, and kits for multifunctional smell assessment. The kits may comprise a first surface adhered by a first releasable adhesive comprising an odorous volatile compound; and the system for registering if the odorous volatile compound is detected by a user. The system or method may comprise queries for obtaining a first input on whether the user detects and identifies the odorous volatile compound, and an intensity by which the odor is perceived.

20 Claims, 6 Drawing Sheets

(52) U.S. Cl.
CPC ........... *A61B 5/7275* (2013.01); *G16H 10/20* (2018.01); *G16H 10/40* (2018.01)

(56) References Cited

U.S. PATENT DOCUMENTS

| | | | | |
|---|---|---|---|---|
| 10,204,176 | B2* | 2/2019 | Sobel | G16H 50/30 |
| 10,667,739 | B2* | 6/2020 | Mochizuki | A61B 5/4011 |
| 10,902,955 | B1* | 1/2021 | Federoff | G16H 50/30 |
| 2002/0139170 | A1* | 10/2002 | Doty | A61B 5/4011 |
| | | | | 73/23.34 |
| 2002/0189608 | A1* | 12/2002 | Raudenbush | A61K 31/045 |
| | | | | 128/200.14 |
| 2003/0113701 | A1* | 6/2003 | Gartner | G09B 3/00 |
| | | | | 434/354 |
| 2007/0077204 | A1* | 4/2007 | Devanand | A61K 49/00 |
| | | | | 424/9.2 |
| 2016/0220165 | A1* | 8/2016 | Taherkhani | A61B 5/4011 |
| 2017/0247145 | A1* | 8/2017 | Reisacher | A61K 8/49 |
| 2017/0290541 | A1* | 10/2017 | Albers | A61B 5/7475 |
| 2017/0364605 | A1* | 12/2017 | Sobel | G16H 40/63 |
| 2019/0021645 | A1* | 1/2019 | Mochizuki | A61B 5/4011 |
| 2020/0253531 | A1* | 8/2020 | Smith | A61B 5/4088 |

OTHER PUBLICATIONS

<https://www.usmellit.com/> (Year: 2021).*
Ann Brauer "One College's Pop-up COVID TestL Stop and 'Smell the Roses' (or the Coffee)" (Year: 2020).*
Mayo Clinic "Smell and Taste Dysfunction in Patients With COVID-19: A Systematic Review and Meta-Analysis" (Year: 2020).*
Sari Koskinen, Seija Vento, Henrik Malmberg & HelyTuorila (2004) Correspondence Between Three Olfactory Tests and Suprathreshold Odor Intensity Ratings, Acta Oto-Laryngologica, 124:9, 1072-1077, DOI: 10.1080/00016480410015776 (Year: 2004).*
S. Nordin, A. Bramerson, C. Murphy & M. Bende (2003) A Scandinavian Adaptation of the Multi-Clinic Smell and Taste Questionnaire: Evaluation of Questions About Olfaction, Acta Oto-Laryngologica, 123:4, 536-542, DOI: 10.1080/00016480310001411 (Year: 2003).*
Ayabe-Kanamura et al., Differences in perception of everyday odors: a Japanese-German cross-cultural study. Chem Senses 23(1):31-38 (1998).
Bhattacharjee et al., Quantitative Assessment of Olfactory Dysfunction Accurately Detects Asymptomatic COVID-19 Carriers. Rochester, NY: Social Science Research Network (2020).
Boesveldt et al., Anosmia-A Clinical Review. Chem Senses 42(7):513-523 (2017).
Brann et al., Non-neuronal expression of SARS-CoV-2 entry genes in the olfactory system suggests mechanisms underlying COVID-19-associated anosmia. Science Advances 6(31): eabc5801 (2020).
Cavazzana et al., Postinfectious olfactory loss: A retrospective study on 791 patients. Laryngoscope 128(1):10-15 (2018).
Choudhury et al., Influences of Age and Sex on a Microencapsulated Odor Memory Test. Chemical Senses 28(9): 799-805 (2003).
Cooper et al., COVID-19 and the Chemical Senses: Supporting Players Take Center Stage. Neuron 107(2): 219-233 (2020).
Croy et al., Olfactory disorders and quality of life—an updated review. Chem Senses 39(3):185-194 (2014).
Dalton et al., Olfactory assessment using the NIH Toolbox. Neurology 80(11 Suppl 3):S32-6 (2013).
Dalton, Olfaction and anosmia in rhinosinusitis. Curr Allergy Asthma Rep 4(3): 230-236 (2004).
Damm et al., Intranasal Volume and Olfactory Function. Chemical Senses 27(9): 831-839 (2002).
Doty et al., Development of the 12-item Cross-Cultural Smell Identification Test (CC-SIT). Laryngoscope 106(3 Pt 1):353-6 (1996).
Doty et al., University of Pennsylvania Smell Identification Test: a rapid quantitative olfactory function test for the clinic. Laryngoscope 94(2 Pt 1):176-8 (1984).
Erskine et al., An unmet need: Patients with smell and taste disorders. Clin Otolaryngol 45(2):197-203 (2020).
Freiherr et al., The 40-item Monell Extended Sniffin' Sticks Identification Test (MONEX-40). J Neurosci Methods 205(1):10-16 (2012).
Gerkin et al., Recent smell loss is the best predictor of COVID-19: a preregistered, cross-sectional study. Medrxiv : the Preprint Server for Health Sciences, Jul. 25, 2020.
Hannum et al., Objective sensory testing methods reveal a higher prevalence of olfactory loss in COVID-19-positive patients compared to subjective methods: A systematic review and meta-analysis. Version 1. medRxiv. Preprint (2020).
Hedner et al., Cognitive factors in odor detection, odor discrimination, and odor identification tasks. J Clin Exp Neuropsychol 32(10):1062-1067 (2010).
Jackman et al., Utility of a three-item smell identification test in detecting olfactory dysfunction. Laryngoscope 115(12):2209-12 (2005).
Kollndorfer et al., Self-esteem as an important factor in quality of life and depressive symptoms in anosmia: A pilot study. Clin Otolaryngol 42(6):1229-1234 (2017).
Laska et al., Trigeminal Perception of Odorant Quality in Congenitally Anosmic Subjects. Chemical Senses 22(4): 447-456 (1997).
Letizia et al., SARS-CoV-2 Transmission among Marine Recruits during Quarantine. N Engl J Med 383(25):2407-2416 (2020).
Liu et al., Odor Mixtures in Identification Testing Using Sniffin' Sticks: The SSomix Test. Scientific Reports vol. 10, Article No. 8155 (2020).
McGann, Poor human olfaction is a 19th-century myth. Science 356(6338): eaam7263 (2017).
Menni et al., Real-time tracking of self-reported symptoms to predict potential COVID-19. Nat Med 26(7):1037-1040 (2020).
Menon et al., Normative Performance on the Brief Smell Identification Test (BSIT) in a Multi-Ethnic Bilingual Cohort: A Project FRONTIER Study. Clin Neuropsychol 27(6): 946-961 (2013).
Morey et al., BayesFactor: Computation of Bayes Factors for Common Designs. (2018).
Neuland et al., Health-related and specific olfaction-related quality of life in patients with chronic functional anosmia or severe hyposmia. Laryngoscope 121(4):867-872 (2011).
Nordin et al., Complaints of olfactory disorders: epidemiology, assessment and clinical implications. Curr Opin Allergy Clin Immunol 8(1):10-15 (2008).
One College's Pop up COVID Test: Stop and Smell the Roses (or the Coffee). 2021.
Paltiel et al., Assessment of SARS-CoV-2 Screening Strategies to Permit the Safe Reopening of College Campuses in the United States. JAMA Network Open 3(7):e2016818 (2020).
Parma et al., SCENTinel 1.0: development of a rapid test to screen for smell loss. Chem Senses (2021).
Pellegrino et al., Corona Viruses and the Chemical Senses: Past, Present, and Future. Chem Senses bjaa031 (2020).
Peterson et al., Three Quarters of People with SARS-CoV-2 Infection are Asymptomatic: Analysis of English Household Survey Data. Clinical Epidemiology 12: 1039-1043 (2020).
R Core, T. 2020. R: A language and environment for statistical computing.
Rabin et al., Odor recognition: familiarity, identifiability, and encoding consistency. J Exp Psychol Learn Mem Cogn 10(2):316-25 (1984).
Rawal et al., The Taste and Smell Protocol in the 2011-2014 US National Health and Nutrition Examination Survey (NHANES): Test-Retest Reliability and Validity Testing. Chemosens Percept 8(3): 138-148 (2015).
Rodriguez et al., Innate immune signaling in the olfactory epithelium reduces odorant receptor levels: modeling transient smell loss in COVID-19 patients. medRxiv (2020).
Roland et al., Smell and taste symptom-based predictive model for COVID-19 diagnosis. Int Forum Allergy Rhinol 10(7):832-838 (2020).
Schonbrodt et al., Sequential hypothesis testing with Bayes factors: Efficiently testing mean differences. Psychol Methods 22(2):322-339 (2017).

(56) References Cited

OTHER PUBLICATIONS

Sorokowski et al., Sex Differences in Human Olfaction: A Meta-Analysis. Front Psychol 10: 242 (2019).

Temmel et al., Characteristics of olfactory disorders in relation to major causes of olfactory loss. Arch Otolaryngol Head Neck Surg 128(6):635-41 (2002).

Wilson et al., Odor identification and decline in different cognitive domains in old age. Neuroepidemiology 26(2):61-67 (2006).

Yan et al., Association of chemosensory dysfunction and COVID-19 in patients presenting with influenza-like symptoms. Int Forum Allergy Rhinol 10(7):806-813 (2020).

Zernecke et al., Comparison of two different odorants in an olfactory detection threshold test of the Sniffin' Sticks. Rhinology 48(3):368-373 (2010).

Gerkin et al., Recent Smell Loss is the Best Predictor of COVID-19 Among Individuals with Recent Respiratory Symptoms. Chemical Senses 46: 1-12 (2021).

Hannum et al., Objective Sensory Testing Methods Reveal a Higher Prevalence of Olfactory Loss in COVID-19-Positive Patients Compared to Subjective Methods: A Systematic Review and Meta-Analysis. Chemical Senses 45: 865-874 (2020).

\* cited by examiner

MULTIFUNCTIONAL SMELL TEST

CROSS-REFERENCE

This application claims the benefit of U.S. Provisional Application No. 63/092,983, filed Oct. 16, 2020, which application is incorporated herein by reference.

BACKGROUND

Smell may be an important indicator of a disease or disorder. Improved smell tests are needed to aid in diagnosing or screening for such diseases or disorders.

SUMMARY

Disclosed herein, in some embodiments, are multifunctional smell assessment kits. The kit may include: a first surface adhered by a first releasable adhesive comprising an odorous volatile compound; and/or a system for registering if said odorous volatile compound is detected by a user, comprising: (a) a first query for obtaining a first input on whether the user detects, by olfaction, the odorous volatile compound, (b) a second query for obtaining a second input on whether the user identifies the odor of the volatile compound, and/or (c) a third query for obtaining a third input on an intensity of the odor as perceived by the user, wherein (a), (b) and (c) may be in any order. Some embodiments include a second surface adhered by a second releasable adhesive not comprising the odorous volatile compound. In some embodiments, the first surface or the second surface comprises plastic, rubber, silicone, or paper. In some embodiments, the first or second releasable adhesive comprises a glue, a resin, a rubber adhesive, or an acrylic adhesive. Some embodiments include a panel adhered directly or indirectly to the first and second surfaces by the first and second releasable adhesives. In some embodiments, the panel comprises paper, card stock, plastic, rubber, metal, or silicone. In some embodiments, the first releasable adhesive temporarily adheres the first surface directly or indirectly to the panel while retaining the odorous volatile compound. In some embodiments, the panel comprises a printed symbol or code indicative of the odor, or indicative of which whether the first or the second releasable adhesive not comprising the odorous volatile compound. In some embodiments, the panel is indirectly adhered to the first and second surfaces, the first releasable adhesive is directly adhered to a third surface directly adhered to the panel, and the second releasable adhesive is directly adhered to a fourth surface directly adhered to the panel. In some embodiments, the system comprises a first computer generated output comprising the first query, a second computer generated output comprising the second query, and a third computer generated output comprising the third query.

Disclosed herein, in some embodiments, are smell assessment methods. The method may include: administering a questionnaire to a subject suspected of having an olfactory impairment; wherein the subject has received a panel comprising a first peelable surface adhered directly or indirectly to the panel by a first adhesive comprising an odorous volatile compound detectible by a person of ordinary olfactory ability, and undetectable by a person having an olfactory impairment, wherein the compound comprises an odor detectable by the person of ordinary olfactory ability and unidentifiable by the person having the olfactory impairment, and/or wherein the panel comprises a second peelable surface adhered directly or indirectly to the panel by a second adhesive not comprising the odorous volatile compound. The questionnaire may include a first question or instruction for determining whether the subject detects, by olfaction, the odorous volatile compound in the first adhesive, a second question or instruction for determining whether the subject identifies the odor of the volatile compound, and a third question or instruction for determining an intensity of the odor as perceived by the subject. In some embodiments, the first question or instruction comprises a question or instruction to determine which of the first peelable surface and the second peelable surface the subject considers to comprise a stronger odor. In some embodiments, the second question or instruction comprises a question or instruction to determine which of a first image or a second image comprises an image corresponding to the odor, wherein the first image comprises an image corresponding to the odor, and wherein the second image comprises an image not corresponding to the odor. In some embodiments, the third question or instruction comprises a question or instruction to determine a quantitation of the intensity of the odor as perceived by the subject. Some embodiments include: identifying the subject as having the olfactory impairment or as having the olfactory impairment based on the subject's response to the first, second, or third question or instruction. Some embodiments include: identifying the subject as likely to have a disease or disorder when the subject is identified as having the olfactory impairment, and identifying the subject as unlikely to have the disease or disorder when the subject is identified as not having the olfactory impairment. In some embodiments, the disease or disorder comprises coronavirus disease 2019 (COVID-19). Some embodiments include administering to the subject a COVID-19 treatment. In some embodiments, the disease or disorder comprises a traumatic brain injury, Parkinson's disease or Alzheimer's disease. Some embodiments include administering to the subject a traumatic brain injury treatment, Parkinson's disease treatment or an Alzheimer's disease treatment.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
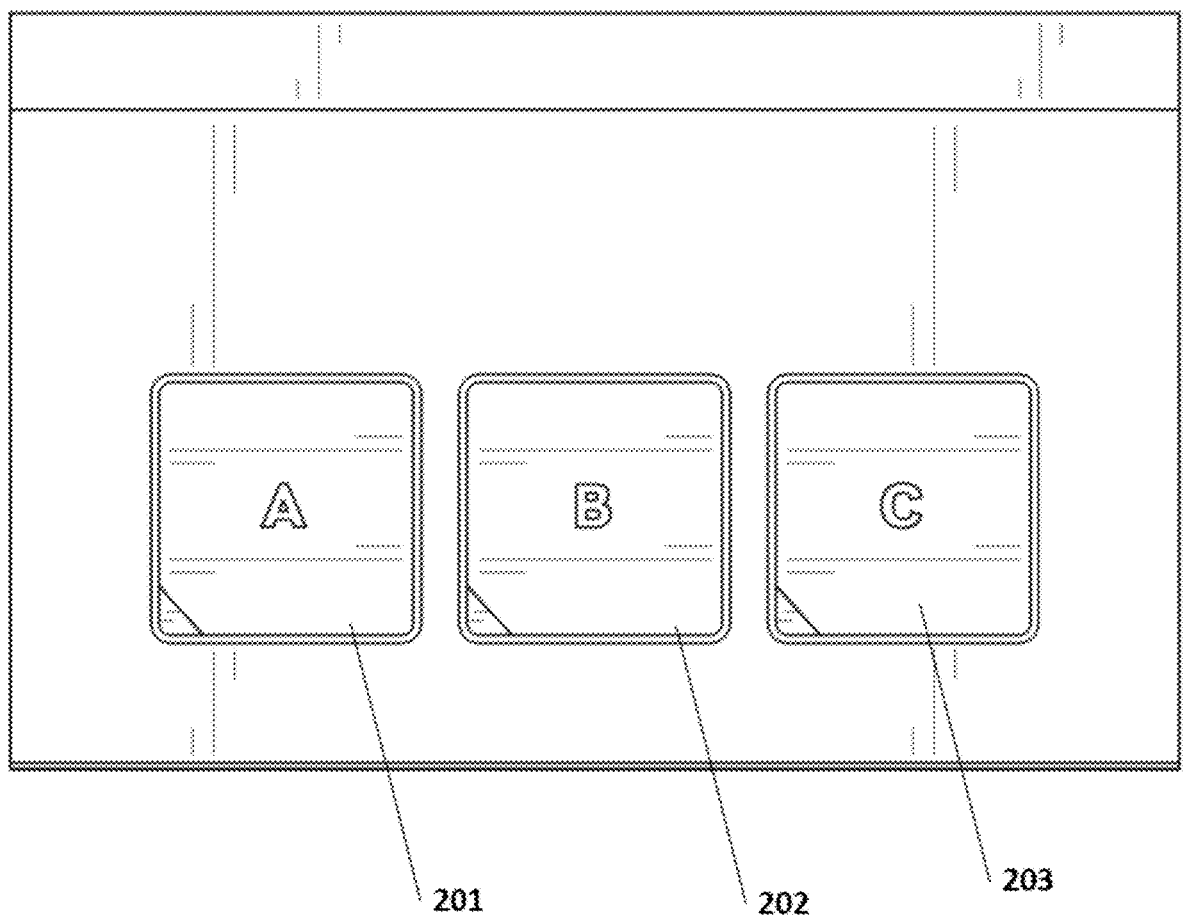
FIG. 1 shows a schematic illustration of a panel of a multifunctional smell assessment kit, in accordance to some embodiments.

Diseases such as respiratory viral infections can temporarily or permanently affect human's sense of smell. Despite how common sudden onset of smell loss is in people with some diseases such as COVID-19, the sense of smell is rarely evaluated in routine medical care, which can have significant negative clinical implication.

The failure to see the mainstream clinical potential of evaluating the sense of smell is due to both theoretical and practical factors. There is a lack of routine and rapid measures of the sense of smell available in the art. However, for COVID-19 surveillance, such routine and rapid smell tests may help identify infected individuals. There are several ways to measure olfaction, to see if a person can (a) detect the presence of an odorant, (b) experience the intensity of an odorant at higher concentration, or can correctly (c) identify the odorant. Existing smell tests typically only measure a single aspect of olfaction, e.g., odorant identification. However, odor identification tasks may be the most sensitive among olfactory skills to cognitive deficits (e.g., verbal memory impairment) which could result in impaired performance for non-sensory reasons. Odorant identification alone may fail to detect the reduction in intensity (especially among young people that may have lost much ability to smell but retain enough to guess the odorant). Indeed, odor intensity, even when self-reported, has proven to be the most predictive indicator of a COVID-19 diagnosis. Indeed, an odor detection, intensity, or identification test can reveal whether an individual suffers from complete smell loss (anosmia). Yet, if their sense of smell is only partially diminished (hyposmia) or distorted (parosmia), testing different smell functions would provide divergent results. For example, a person with hyposmia may or may not identify a target odor but may identify an odor's intensity. Additionally, a person with parosmia may detect and rate the intensity of an odor but may fail at odor identification.

Recognized herein is a need to develop a smell test that assesses multiple olfactory functions in order to provide a robust, yet rapid assessment of smell loss which can be optimized for routine use and ad hoc population surveillance.

Multifunctional Smell Assessment

Olfactory Assessment Kit

Disclosed herein, in some cases, are multifunctional smell assessment kits. The kit may include three odor labels adhered to a backing. The three odor labels may each include an outward surface (e.g. a flat plastic surface) adhered by an adhesive to another surface or backing. For example, the adhesive may be directly adhered to another surface (e.g. another flat plastic surface) that is directly adhered to a panel or backing (e.g., as shown and described in FIG. 4 and FIG. 5). Also possible are embodiments that include the adhesive directly adhered to the panel or backing. One of the odor labels may include an odorous compound within the adhesive, while the other two odor labels do not include the odorous compound. The odor labels may also be referred to as, or include, an odor sticker or smell sticker. The odor labels may include plastic, rubber, silicone, paper, or another material. The adhesive may include a glue, a resin, a rubber adhesive, an acrylic adhesive, or any other adhesive capable of retaining an odorous compound for use in the smell assessment. The panel or backing may include paper, card stock, plastic, rubber, metal, silicone, or another material. This kit may be used to retain the odor within the adhesive of one of the odor labels for an extended period of time, while releasing the odor to a user in a uniform, predictable way when the odor label is peeled away from the panel or backing.

The kit including the three odor labels bound either directly or indirectly to a backing allows for a simple system or method of smell assessment that includes three queries in any order to determine if a user has a smell impairment. The three queries may identify whether the user detects the odorous compound, whether the user identifies the odor of the odorous compound, and an intensity by which the user perceives the odor (if the user perceives the odor at all). The kit along with these three queries may aid in smell assessment without the need for a multitude of smells or other complexities.

Disclosed herein, in some cases, are odor kits for smell assessment. The odor kit may be a multifunctional smell assessment kit. The multifunctional smell assessment kit may comprise at least two surfaces (e.g. three surfaces) adhered to each other by a first releasable matrix (e.g. adhesive) which may contain an odorous volatile compound. The first surface adhered by a first releasable matrix comprising an odorous volatile compound may be referred to as an odor sticker or an odor label. The odor label may contain an odor released when the two surfaces are separated, or may be a blank, containing minimal odorous volatile compound. In some cases only one of the surfaces is adhered using the adhesive with the odorous volatile compound, while the other(s) are adhered using the same or similar adhesive but without the odorous volatile compound. Some embodiments include a first and second releasable matrix (in any order). In some cases, the second releasable matrix may not release a volatile compound detectable through olfaction. The multifunctional smell assessment kit may comprise 1, 2, 3, 4, 5, 6, 7, 8, 9, 10, or more smell stickers. The multifunctional smell assessment kit may comprise 1, 2, 3, 4, 5, 6, 7, 8, 9, 10, or more odorous volatile compounds.

The first releasable matrix may be a first releasable matrix (e.g. adhesive). The second releasable matrix may be a second releasable adhesive. The first surface and/or the second surface may comprise plastic, rubber, silicone, or paper. The first or second releasable matrix may comprise a glue, a resin, a rubber adhesive, or an acrylic adhesive. The first releasable matrix may comprise an oil comprising the odorous volatile compound. The odor may comprise a familiar household odor. For example, the odor may comprise a rose, a popcorn, a coffee, orange, coconut, strawberry, banana, or a chocolate odor. Other examples include butter, fruit, lemon, or soap.

The odor may be selected from a number of odors. For example, a group of smell tests may be manufactured that comprise any of 1, 2, 3, 4, 5, 6, 7, 8, 9, 10, 11, 12, 13, 14, 15, or more smells, wherein each smell test includes one smell (although some embodiments may include more than one smell per kit). This may allow the tests to be used without the subject being able to guess what the smell is, particularly if the subject has had the test before and know what one or more of the possible smells is. The system may include multiple queries that provide increased discrimination power that may allow for use of a limited number smells within the group of smell tests. The group of smell tests may be manufactured that comprise no more than 1, 2, 3, 4, 5, 6, 7, 8, 9, 10, 11, 12, 13, 14, or 15, smells, wherein each smell test includes only one smell. For example, the group of smell tests may include no more than 4 or 8 smells, whereas existing smell tests may need a greater number of possible smells within a group of tests.

The multifunctional smell assessment kit may further comprise a series of odor labels adhered to a panel to provide a support structure. The panel may comprise paper, card stock, plastic, rubber, metal, or silicone. The odor label may adhere the support structure while retaining the odorous volatile compound. In some cases, an intensity of the odor of the volatile compound does not diminish while the odor label adheres the first surface to the support structure for a period of time. In some cases, the intensity of the odor of the volatile compound does not significantly diminish when the first releasable matrix re-adheres the first surface to the panel after the first surface is being peeled away from the support structure and re-adhered to the support structure. The panel may comprise at least 1, 2, 3, 4, 5, 6, 7, 8, 9, or 10 surface areas configured to adhere a surface and/or a releasable matrix. The odor kit may comprise a peeling layer disposed on top of a surface area of the panel. In some cases, at least a portion of the peeling layer is removably coupled to the panel (or support structure). Uncoupling a portion of a peeling layer from the panel (or support structure) may release a volatile compound detectable through olfaction. The peel and smell technology described herein is useful because it keeps the odorous compound fresh. This way the compound or odor of the compound does not diminish quickly over time, and the smell test can be used multiple times, or the odor may be delivered consistently. In some cases, the smell test may be re-used 1, 2, 3, 4, 5, 6, 7, 8, 9, or 10 times, or more, or a range of times defined by any two of the aforementioned integers. The consistency of odor delivery allows for the use of an intensity query by which the user rates the intensity of smell detected or perceived. The panel or support structure may be a backing such as a paper backing.

In some embodiments, an odor label comprises or consists of a single surface and the releasable adhesive. The odor label may be adhered to a support panel by means of the adhesive. The releasable adhesive may include the odorous volatile compound.

In some cases, the kit includes three odor labels. The odor labels may be indirectly adhered to the panel. For example, three odor labels may be adhered to one or more other surfaces (e.g. plastic surfaces) adhered to a panel or backing. Some such embodiments include a first surface (e.g. odor label) adhered by an adhesive with an odorous compound to another surface that is directly adhered to the panel or backing. Some embodiments include a second and third surface (e.g. second and third odor labels, in any order) each adhered by an adhesive without the odorous compound to other surfaces that are directly adhered to the panel or backing.

Figure 4:
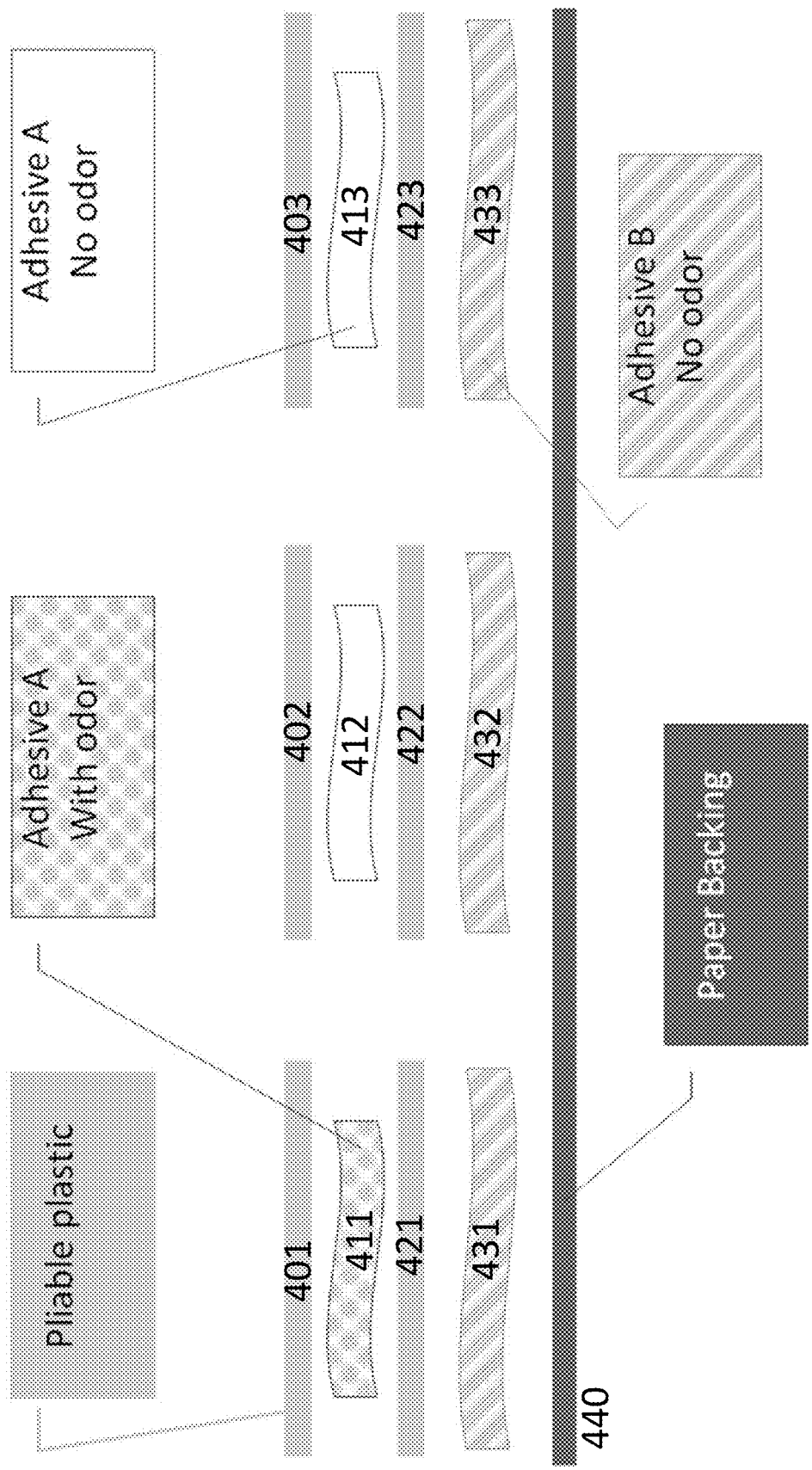
FIG. 4 shows various components of a smell assessment kit.
Figure 5:
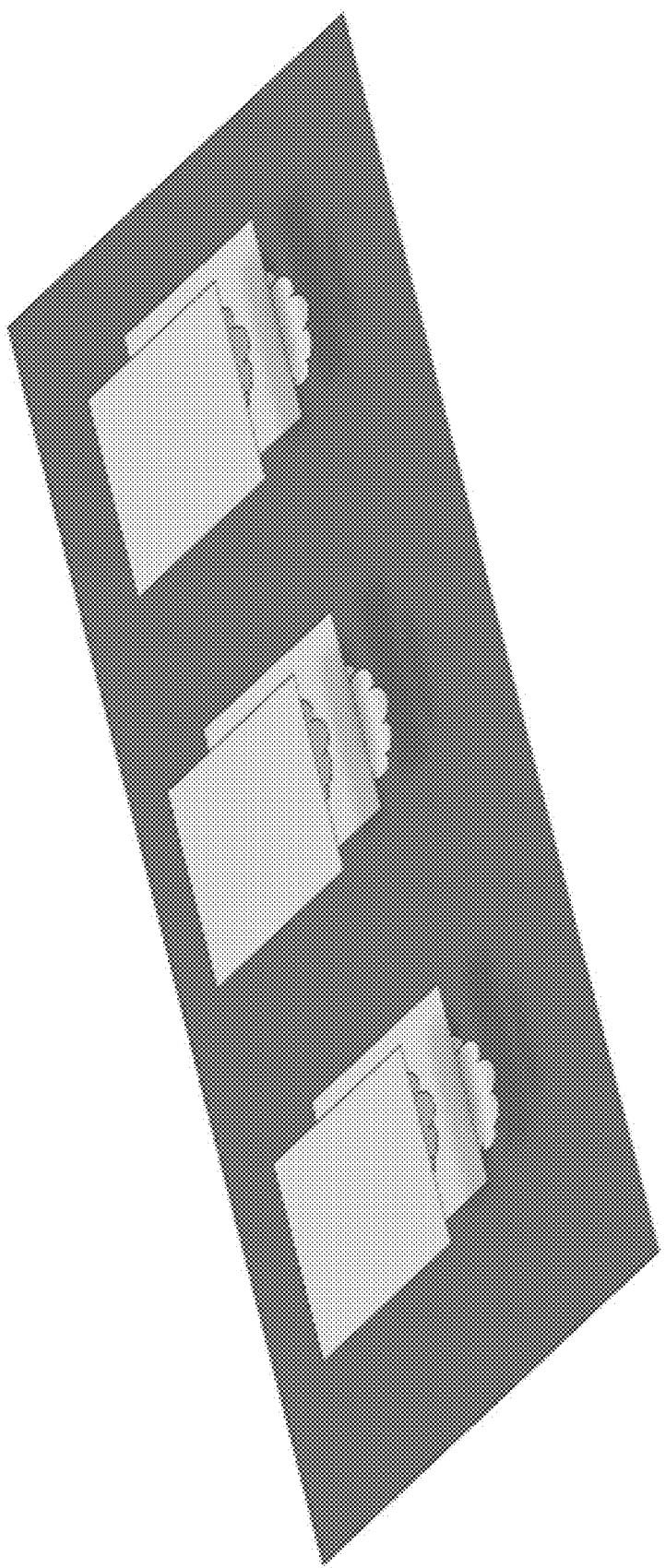
FIG. 5 shows various components of a smell assessment kit.

Some embodiments include any of the components shown in FIG. 4. The kit may include a first surface 401 adhered by an adhesive 411 comprising an odorous compound (e.g. odor label 1). The kit may include a second surface 402 adhered by an adhesive 412 not comprising the odorous compound (e.g. odor label 2). The kit may include a third surface 403 adhered by an adhesive 413 not comprising the odorous compound (e.g. odor label 3). Odor labels 1-3 may all include the same adhesive but for the odorous compound. The adhesive 411 of odor label 1 may be further adhered to a fourth surface 421. The adhesive 412 of odor label 2 may be further adhered to a fifth surface 422. The adhesive 413 of odor label 3 may be further adhered to a sixth surface 423. The fourth surface 421 may be adhered by an adhesive 431 to a panel 440. The fifth surface 422 may be adhered by an adhesive 432 to the panel 440. The sixth surface 423 may be adhered by an adhesive 433 to the panel 440. The adhesives adhering the fourth, fifth, or sixth surfaces to the panel may all be the same type of adhesive as each other. The adhesives adhering the fourth, fifth, and/or sixth surfaces to the panel may all be the same type of adhesive as the adhesives of the first, second, and/or third odor labels but for the odorous compound. For example, in some cases only the adhesive of the first odor label contains the odorous compound. In some alternatives, the first, second, and third odor labels are all directly adhered to a single surface that is adhered to the panel, whereas in other cases the first, second, and third odor labels are all directly adhered to separate surfaces that are adhered to the panel. Note that the terms first, second, third, fourth, fifth, and sixth are used for convention, and do not necessarily denote a specific order. For example, the first, second, and third odor labels may be in any order, or in any placement on the panel.

In some cases, only one odor is used per smell test kit. For example, a backing may include only one odor label comprising an odorous compound, whereas previous smell tests may include more than one odor. A combination of multiple queries enables the use of only one odor.

FIG. 1 shows a panel with a first surface adhered by a first releasable matrix 201, a second surface adhered by a second releasable matrix 202, a third surface adhered by a third releasable matrix 203. The first releasable matrix and the second releasable matrix may each comprise an odorous volatile compound. The third releasable matrix may not an odorous volatile compound. The third releasable matrix may a compound that is not odorous.

Figure 2:
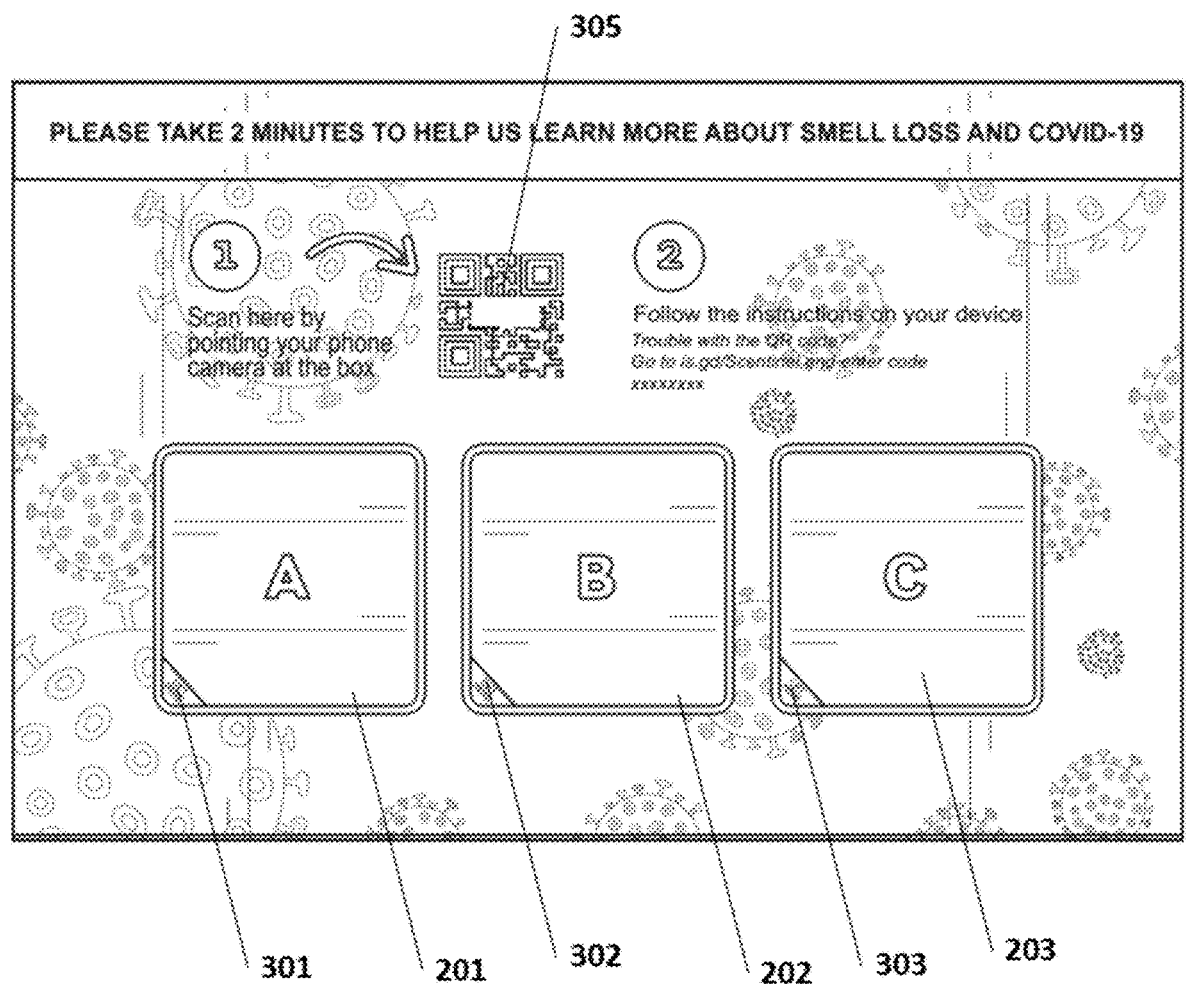
FIG. 2 shows a schematic illustration of a panel of a multifunctional smell assessment kit with a releasable adhesive, in accordance to some embodiments.

FIG. 2 shows another schematic illustration of a panel of a multifunctional smell assessment kit comprising peeling features and a symbol or code. The first releasable matrix 201 may be peeled using a peeling element 301. The second releasable matrix 202 may be peeled using a peeling element 302. The third releasable matrix 203 may be peeled using a peeling element 303. The panel may comprise a symbol or code 305.

Figure 3:
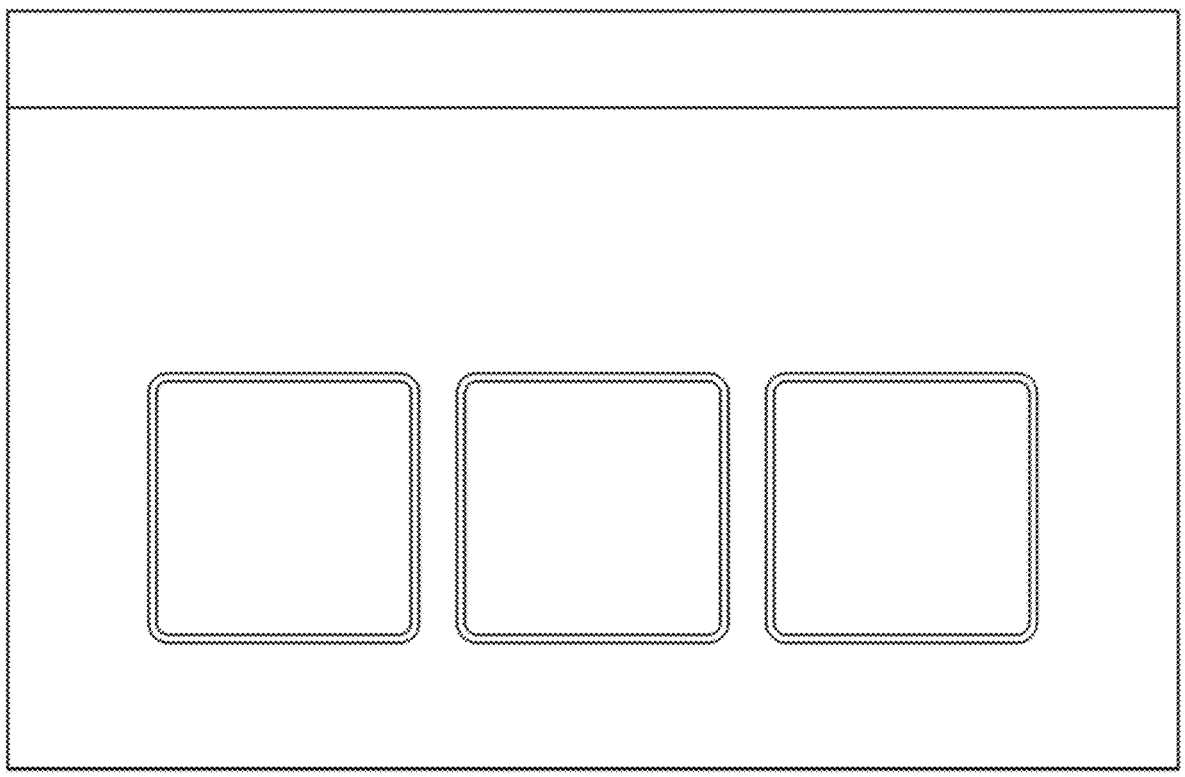
FIG. 3 shows a smell test design.

FIG. 3 shows an ornamental design for a smell test. Some embodiments include the ornamental design as shown in FIG. 3.

The odor kit may further comprise a multifunctional smell assessment system. The system may comprise registering if the odorous volatile compound is detected by a user. The registering may comprise a first query for obtaining a first input on whether the user detects, by olfaction, the odorous volatile compound. The first input on whether the user detects, by olfaction, the odorous volatile compound may comprise a determination of which of the odor labels on the panel is considered odorous by the user. A user can consider any of the odor labels on the panel to attempt to detect, by olfaction, the odorous volatile compound of that surface. The user may consider a first surface or a second surface each comprising an odor of a volatile compound. The registering may comprise a second query for obtaining a second input on whether the user identifies the odor of the volatile compound. The second query may comprise a first image corresponding to the odor, and a second image not corresponding to the odor. The second input on whether the user identifies the odor may comprise a selection of the first image corresponding to the odor, or a selection of the second image not corresponding to the odor. The registering may comprise a third query for obtaining a third input on an intensity of the odor as perceived by the user. The third query may comprise a questionnaire associated with an intensity of the odor. The third input on the intensity of the odor as perceived by the user, may comprise a quantitation of the intensity of the odor. The queries need not occur in the order presented herein. For example, the second or third query may be presented to the user first, or the first or second query may be presented to the user last.

The multifunctional smell assessment kit may further comprise a network over which the first input is transmitted. The multifunctional smell assessment kit may further comprise a network over which the second input is transmitted. The multifunctional smell assessment kit may further comprise a network over which a third input is transmitted. The inputs may be obtained or transmitted in any order.

A user with a compromised sense of smell may be unable to detect or localize, by olfaction, the odorous volatile compound. The user with a compromised sense of smell may be unable to is unable to identify the odor. For example, a user with a compromised sense of smell may be unable to pick an image (e.g., image of a banana) associated with a smell (e.g., smell of banana). The user with a compromised sense of smell may be unable to perceives the odor below a designated intensity. The designated intensity may be at about 20 on a scale of 0-100, or may be at about 2 on a scale of 0-10. The designated intensity may be at least about 20 on a scale of 0-100, or may be at least about 2 on a scale of 0-10.

The query may be delivered orally, in written form, or by a computational device or telephone (e.g. smart phone). The system for registering if the odorous volatile compound is detected by a user may comprise a symbol or code. The symbol or code is printed on the panel. The symbol or code may comprise a quick response (QR) code or a web address. The symbol or code may be indicative of the composition of the odor labels. The symbol or code may be indicative that a first releasable matrix releases a first smell. The symbol or code may indicate a smell that a surface of a panel releases. The system may comprise a computer or an operator that may be configured to read the symbol or code to generate an output of a query.

The system may comprise a first output comprising the first query. The system may comprise a second output comprising the second query. The system may comprise a third output comprising the third query. The output may be a computer generate output.

The multifunctional smell assessment kit may further comprise a network over which the first output is transmitted. The multifunctional smell assessment kit may further comprise a network over which the second output is transmitted. The multifunctional smell assessment kit may further comprise a network over which a third output is transmitted.

The multifunctional smell assessment kit may further comprise a computational device comprising an output device configured to indicate an output. The output may indicate that the user may not have a compromised sense of smell when the first input indicates that the odorous volatile compound is detected by the user. The output may indicate that the user may not have a compromised sense of smell when the second input indicates that the odor is identified by the user. The output may indicate that the user may not have a compromised sense of smell when the third input indicates that the intensity of the odor is perceived by the user at or above the threshold intensity. The output may indicate that the user may not have a compromised sense of smell when the first input indicates that the odorous volatile compound is detected by the user, the second input indicates that the odor is identified by the user, and the third input indicates that the intensity of the odor is perceived by the user at or above the threshold intensity. The computational device may comprise a telephone (e.g. smart phone) or tablet.

The user with a compromised sense of smell may have a coronavirus infection, a neurodegenerative disease, a head trauma, a cognitive impairment, or anosmia, that results in the compromised sense of smell. In some embodiments, the test detects anosmia in the subject. "Anosmia" may be used in the broad general sense, or in the narrow sense used medically.

Olfactory Assessment System

Also disclosed herein, in some cases, are systems for multifunctional smell assessment. The system may comprise an odor kit. The odor kit may comprise a support structure comprising a first surface area. The odor kit may further comprise a first peeling layer disposed on top of the first surface area. At least a portion of the first peeling layer may be removably coupled to the support structure. The odor kit may further comprise a chemical substance disposed between the first peeling layer and first surface area. Uncoupling the portion of the first peeling layer from the support structure may release a volatile compound. The volatile compound may be detectable through olfaction. The system may further comprise a first module for receiving a first input from a user. The first input may correlate whether the user detected the volatile compound through olfaction upon uncoupling the portion of the first peeling layer. The first module may receive the first input through a user interface. The system may further comprise a second module for receiving a second input from a user. The second input may correlate whether the user identified a type of odor corresponding to the volatile compound upon uncoupling the portion of the first peeling layer. The second module may receive the second input through the user interface. The system may further comprise a third module for receiving a third input from a user. The third input may correlate to an intensity level provided by the user for the type of odor. The third module may receive the third input through the user interface. The system may further comprise a fourth module for determining an olfaction capability by the user based on the first input, the second input, and the third input. The fourth module can generate an output based on the determined olfaction capability. The first module, the second module, the third module, or the fourth module can be performed by a user.

The system may comprise a computer-implemented system. The computer-implemented system may comprise a first module for receiving a first input from a user. The first input may correlate whether the user detected the volatile compound through olfaction upon uncoupling the portion of the first peeling layer. The first module may receive the first input through a user interface. The computer-implemented system may further comprise a second module for receiving a second input from a user. The second input may correlate whether the user identified a type of odor corresponding to the volatile compound upon uncoupling the portion of the first peeling layer. The second module may receive the second input through the user interface. The computer-implemented system may further comprise a third module for receiving a third input from a user. The third input may correlate to an intensity level provided by the user for the type of odor. The third module may receive the third input through the user interface. The computer-implemented system may further comprise a fourth module for determining an olfaction capability by the user based on the first input, the second input, and the third input. The fourth module can generate an output based on the determined olfaction capability.

Also disclosed herein, in some cases, are smell detection systems. The system may comprise a panel comprising a first peelable surface adhered to the panel by a first adhesive matrix. The adhesive matrix may comprise an adhesive. The adhesive matrix may comprise a volatile compound configured to be detected by a person of ordinary olfactory sensitivity, and configured to be undetectable by a person having an impaired olfactory sensitivity. The first adhesive matrix may be an adhesive comprising the volatile compound. The compound may comprise an odor identifiable by the person of ordinary olfactory sensitivity and unidentifiable by the person having the impaired olfactory sensitivity. The system may further comprise a symbol or code identifiable by a computational device. The symbol or code may be configured to obtain a first input on whether the volatile compound is detected in the first adhesive matrix, a second input on whether the odor is identified, and a third input on a perceived intensity of the odor.

Olfactory Assessment Method

Also disclosed herein, in some cases, are smell assessment methods. The method may be used to identify an olfactory impairment in a subject. The subject may be suspected of having the olfactory impairment. The subject may have received a panel comprising a first peelable surface adhered to the panel by a first adhesive matrix. The first peelable surface and/or the first adhesive matrix may comprise an odorous volatile compound detectible by a person of ordinary olfactory ability, and undetectable by a person having an olfactory impairment. The compound may comprise an odor detectable by the person of ordinary olfactory ability and unidentifiable by the person having the olfactory impairment. The panel may comprise a second peelable surface adhered to the panel by a second adhesive matrix. The second peelable surface and/or the second adhesive matrix may not comprise an odorous volatile compound.

The method may comprise obtaining information about the subject. The information obtained may relate to a first question or instruction, a second question or instruction, and a third question or instruction (in any order). Some embodiments include obtaining information from the subject on whether the subject detects, by olfaction, the odorous volatile compound in the first adhesive matrix. Some embodiments include obtaining information from the subject on whether the subject identifies the odor of the volatile compound. Some embodiments include obtaining information from the subject on an intensity of the odor as perceived by the subject.

The method may comprise administering a questionnaire to a subject. The questionnaire may comprise a first question or instruction, a second question or instruction, and a third question or instruction (in any order). The first question or instruction may be designed for determining whether the subject detects, by olfaction, the odorous volatile compound in the first adhesive matrix. The second question or instruction may be designed for determining whether the subject identifies the odor of the volatile compound. The third question or instruction may be designed for determining an intensity of the odor as perceived by the subject. The first question or instruction may comprise a question or instruction to determine which of the first peelable surface and the second peelable surface the subject considers to comprise a stronger odor. The second question or instruction may comprise a question or instruction to determine which of a first image or a second image may comprise an image corresponding to the odor. In some cases, the first image may comprise an image corresponding to the odor. In some cases, the second image may comprise an image not corresponding to the odor. The third question or instruction may comprise a question or instruction to determine a quantitation of the intensity of the odor as perceived by the subject. The question or instruction to determine a quantitation of the intensity of the odor as perceived by the subject may comprise an image of a slider. The quantitation of the intensity of the odor as perceived by the subject may comprise a scale of 0-10. The quantitation of the intensity of the odor as perceived by the subject may comprise a scale of 1-10. The quantitation of the intensity of the odor as perceived by the subject may comprise a scale of 0-100. The quantitation of the intensity of the odor as perceived by the subject may comprise a scale of 1-100.

The smell assessment method may further comprise determining whether the subject detects, by olfaction, the odorous volatile compound in the first adhesive matrix based on the subject's response to the first question or instruction, determining whether the subject identifies the odor based on the subject's response to the second question or instruction, and determining whether an intensity of the odor as perceived by the subject based on the subject's response to the third question or instruction.

The smell assessment method may further comprise identifying the subject as having olfactory impairment when the subject is determined to not detect, by olfaction, the odorous volatile compound in the first adhesive matrix, when the subject is determined to not identify the odor, or when the subject is identified to perceive the intensity of the odor as below a threshold intensity.

The smell assessment method may further comprise identifying the subject as not having an olfactory impairment when the subject is determined to detect, by olfaction, the odorous volatile compound in the first adhesive matrix, when the subject is determined to identify the odor, or when the subject is identified to perceive the intensity of the odor as at or above a threshold intensity.

The smell assessment method may further comprise identifying the subject as having olfactory impairment when the subject is determined to not detect, by olfaction, the odorous volatile compound in the first adhesive matrix, when the subject is determined to not identify the odor, and when the subject is identified to perceive the intensity of the odor as below a threshold intensity.

The smell assessment method may further comprise identifying the subject as likely to have a disease or disorder when the subject is identified as having the olfactory impairment, and identifying the subject as unlikely to have the disease or disorder when the subject is identified as not having the olfactory impairment. The disease or disorder may comprise an infection, a neurodegenerative disorder, or a cognitive impairment. The infection may comprise a coronavirus infection. The smell assessment method may further comprise administering to the subject a coronavirus treatment. The coronavirus infection may comprise coronavirus disease 2019 (COVID-19). The neurodegenerative disorder may comprise Parkinson's disease or Alzheimer's disease. The smell assessment method may further comprise administering to the subject a neurodegenerative disease treatment. The cognitive impairment may have resulted from a head injury. The head injury may comprise a traumatic brain injury. The smell assessment method may further comprise administering to the subject treatment for the head injury. Examples of head injuries include an injury due to collisions such as in an automobile accident or a sports injury. The subject may be a human.

The smell assessment method may further comprise replacing the first peelable surface back on the panel, and re-using the first peelable surface adhered to the panel by the first adhesive matrix comprising the odorous volatile compound in an additional smell test. The additional smell test may be performed on a different subject. The additional smell test may be of the same subject at a later time than the first smell test. The smell assessment method may further comprise replacing the first peelable surface back on the panel, and re-using the first peelable surface adhered to the panel by the first adhesive matrix comprising the odorous volatile compound in 1, 2, 3, 4, 5, 6, 7, 8, 9, 10, 11, 12, 13, 14, or 15, or more, additional smell tests, or in a range of additional smell tests defined by any two of the aforementioned integers. The intensity of the odorous volatile compound may remain substantially constant in additional smell tests.

Also disclosed herein, in some cases, are smell detection methods for detecting an olfactory sensitivity impairment. The method may comprise: (a) providing an odor kit to a subject, (b) uncoupling the portion of the first peeling layer from the support structure by the subject; and (c) administering a questionnaire to the subject. The odor kit may comprise a support structure having a first surface area; a first peeling layer disposed on top of the first surface area; and a chemical substance disposed between the first peeling layer and first surface area. At least a portion of the first peeling layer may be removably coupled to the support structure. Uncoupling the portion of the first peeling layer from the support structure may release a volatile compound detectable through olfaction. In some cases, the questionnaire may comprise a first question or instruction for determining whether the subject detects, by olfaction, the volatile compound upon the uncoupling of step b, a second question or instruction for determining whether the subject identifies a type of odor associated with the volatile compound, and a third question or instruction for determining an intensity of the type of odor as perceived by the subject.

The subject may be considered to fail the smell test if the subject fails 1 of the 3 queries (e.g. if the subject cannot (1) determine which smell label comprises the odor, (2) identify the odor, or (3) perceive the odor above a threshold intensity level). The subject may be considered to fail the smell test if the subject fails 2 of the 3 queries. The subject may be considered to fail the smell test if the subject fails 3 of the 3 queries. The subject may be considered to pass the smell test if the subject fails no more than 1 of the 3 queries. The subject may be considered to pass the smell test if the subject fails no more than 2 of the 3 queries. The subject may be considered to pass the smell test if the subject fails 0 of the 3 queries. In some cases, if the subject fails the test, the subject is considered to have an olfactory impairment. In some cases, if the subject does not fail the test, the subject is not considered to have an olfactory impairment.

Large Scale Deployment of Smell Test for Population Surveillance

At least six considerations may be important for large scale deployment of a smell test: (a) it may need to be fast and simple to administer without trained personnel, (b) easily identified odorants may need to be chosen, (c) there may need to be enough odorants so people can take the test frequently, (d) the way the odorants are offered to participants may be as uniform as possible, (e) the test is designed to avoid physical contamination, and (f) the correct answers may not be not easy to guess. Speed may be important because smell testing especially for population surveillance may be fast, e.g., for building admittance. Odorant choice may be important because the odorants may be familiar within the cultural or geographic context where the test is used, to minimize misattributions that do not depend on the ability to smell. Odorants in some cases may not have a pungent component due to trigeminal activation (e.g. mint and cinnamon) because they can be detected by anosmic individuals. The number of odorants may be important because the test may be repeatedly taken (e.g., each day for several weeks), it may include enough odorants so that people do not give rote answers. Uniformity in how the odorant is delivered may be important (e.g., odorant pens, scratch-and-sniff, etc.) and they may be easily accessed, without tools (e.g., coins which are often used for scratch-and-sniff) and without introducing new sources of variation, e.g., unequal scratching when releasing the odorant. Avoiding physical contamination may be important and participants in some instances may not share the same olfactory stimulus, e.g., odorant-containing pens to reduce the transfer of potential pathogens from nose to hand. Finally, the test structure may need to be robust against guessing. The systems, kits, and methods described herein, may have these benefits.

Multifunctional Smell Assessment Test Design

The multifunctional smell assessment test may take less than 2 minutes measuring odor discrimination, intensity and identification based on one odorant. An example includes a flower odor (e.g. Givaudan, perfume compound with main component 2-phenylethanol, CAS-No. 60-12-8). The test may use odors that are highly familiar to the US population as indicated by published data from existing databases.

The multifunctional smell assessment test may include three odor patches created with a peel and smell sticker glued to a card via an odorless adhesive. This technology may prevent cross-contamination of odor samples on the same card (e.g., useful for an accurate odor detection test), may provide standardization of odor delivery across cards and odors (e.g. useful for an accurate odor intensity test), and may limit residual odor in the air after the test (residual odor in the air could compromise the ability to identify odors).

The test may include olfactory function components that can be objectively assessed to yield a falsification metric and the ability to calculate the probability of passing the test in the absence of smell ability. The smell test odor detection subtest with 3 possibilities may have a guessing probability of 33%. The odor intensity subtest may rely on a subjective experience of the participant and in some instances may not be directly falsified. The odor identification subtest may comprise two possibility: a first try, which is a 4-alternative forced choice task with guessing probability of 25% and a second try, which is a 3-alternative forced choice task with guessing probability of 33%.

Computer Systems

Figure 6:
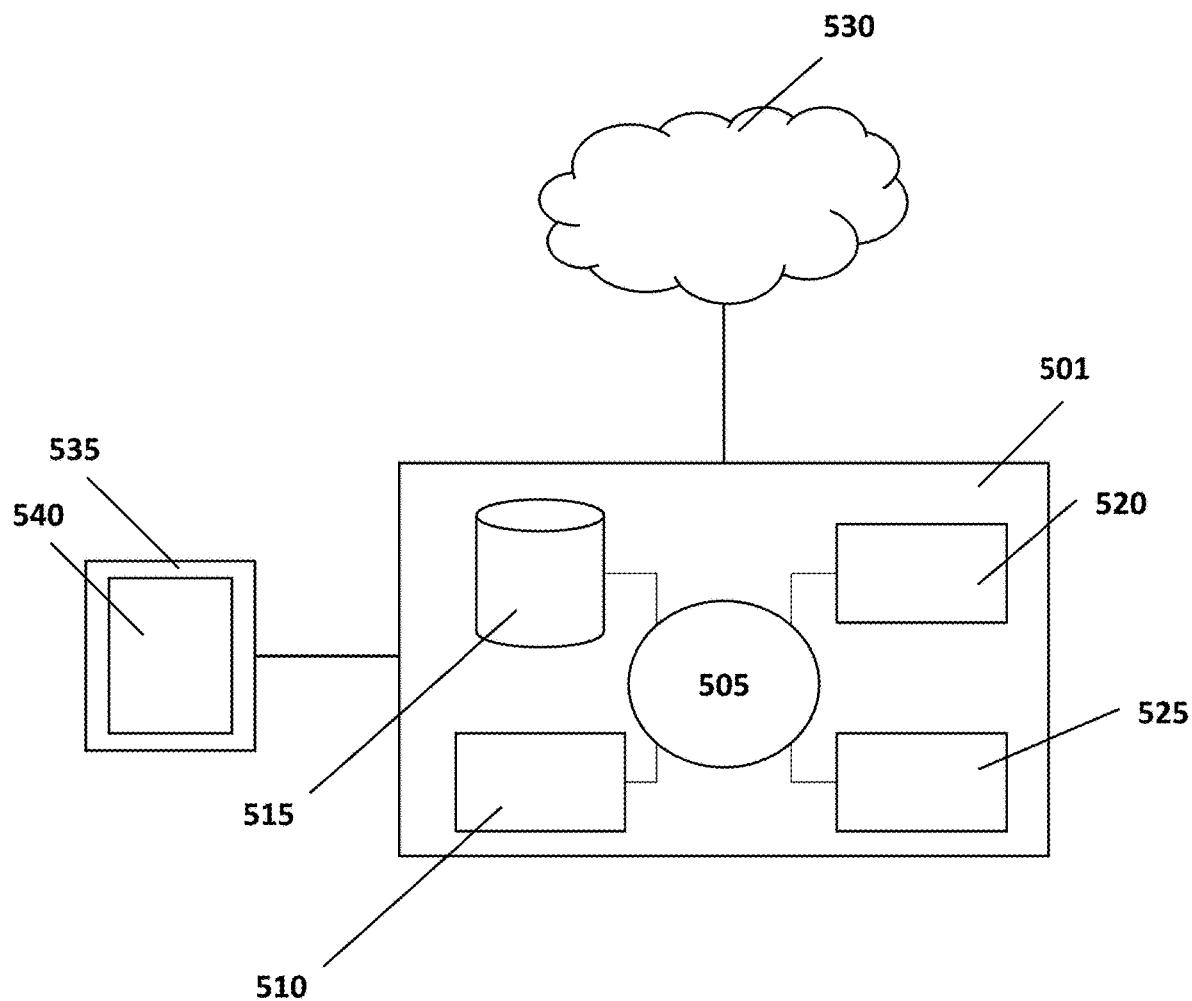
FIG. 6 shows a computer system that is programmed or otherwise configured to implement methods provided herein.

The present disclosure provides computer systems that are programmed to implement methods or systems of the disclosure. FIG. 6 shows a computer system 501 that is programmed or otherwise configured to perform methods described herein. The computer system 501 can regulate various aspects of the present disclosure, such as, for example, receiving a symbol or a code to identify a panel, provide a first, a second, or a third query to obtain a first input, a second input, and/or a third input, generate a first, a second, or a third output, and provide an assessment of the smell test. The computer system 501 can be an electronic device of a user or a computer system that is remotely located with respect to the electronic device. The electronic device can be a mobile electronic device. In some cases, a first input device may be a touch screen, keyboard, or mouse. In some cases, a second input device may be a camera for the code or symbol. The touch screen or other device may include a GUI that has a slider tool (e.g. a ruler type bar where a person moves his or her finger across the screen to select the intensity of smell detected). First, second, and third may be used for convention, and the queries, inputs, and outputs may be in any order.

The computer system 501 includes a central processing unit (CPU, also "processor" and "computer processor"

herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user (e.g., a mobile device). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), specifically designed kiosks, or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

A machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540 for providing, for example, a symbol or a code to identify a panel, provide a first, a second, or a third query to obtain a first input, a second input, and/or a third input, provide a first, a second, or a third output, and provide an assessment of the smell test. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 505. The algorithm can, for example, receive a symbol or a code to identify a panel, provide a first, a second, or a third query to obtain a first input, a second input, and/or a third input, generate a first, a second, or a third output, and provide an assessment of the smell test.

Web Application

In some cases, a computer program includes a web application. In light of the disclosure provided herein, those of skill in the art will recognize that a web application may utilize one or more software frameworks and one or more database systems. A web application, for example, is created upon a software framework such as Microsoft®.NET or Ruby on Rails (RoR). A web application, in some instances, utilizes one or more database systems including, by way of non-limiting examples, relational, non-relational, feature oriented, associative, and XML database systems. Suitable relational database systems include, by way of non-limiting examples, Microsoft® SQL Server, mySQL™, and Oracle®. Those of skill in the art will also recognize that a web application may be written in one or more versions of one or more languages. In some cases, a web application is written in one or more markup languages, presentation definition languages, client-side scripting languages, server-side coding languages, database query languages, or combinations thereof. In some cases, a web application is written to some extent in a markup language such as Hypertext Markup Language (HTML), Extensible Hypertext Markup Language (XHTML), or eXtensible Markup Language (XML). In some cases, a web application is written to some extent in a presentation definition language such as Cascading Style Sheets (CSS). In some cases, a web application is written to some extent in a client-side scripting language such as Asynchronous Javascript and XML (AJAX), Flash® Actionscript, Javascript, or Silverlight®. In some cases, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some cases, a web application is written to some extent in a database query language such as Structured Query Language (SQL). A web application may integrate enterprise server products such as IBM® Lotus Domino®. A web application may include a media player element. A media player element may utilize one or more of many suitable multimedia technologies including, by way of non-limiting examples, Adobe® Flash®, HTML 5, Apple® QuickTime®, Microsoft® Silverlight®, Java™, and Unity®.

Mobile Application

In some instances, a computer program includes a mobile application provided to a mobile digital processing device. The mobile application may be provided to a mobile digital processing device at the time it is manufactured. The mobile application may be provided to a mobile digital processing device via the computer network described herein.

A mobile application is created by techniques known to those of skill in the art using hardware, languages, and development environments known to the art. Those of skill in the art will recognize that mobile applications may be written in several languages. Suitable programming languages include, by way of non-limiting examples, C, C++, C#, Featureive-C, Java™, Javascript, Pascal, Feature Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments may be available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some cases, a computer program includes a standalone application, which is a program that may be run as an independent computer process, not an add-on to an existing process, e.g., not a plug-in. Those of skill in the art will recognize that standalone applications are sometimes compiled. In some instances, a compiler is a computer program (s) that transforms source code written in a programming language into binary feature code such as assembly language or machine code. Suitable compiled programming languages include, by way of non-limiting examples, C, C++, Featureive-C, COBOL, Delphi, Eiffel, Java™, Lisp, Python™, Visual Basic, and VB.NET, or combinations thereof. Compilation may be often performed, at least in part, to create an executable program. In some instances, a computer program includes one or more executable complied applications.

Web Browser Plug-In

A computer program, in some aspects, includes a web browser plug-in. In computing, a plug-in, in some instances, is one or more software components that add specific functionality to a larger software application. Makers of software applications may support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. The toolbar may comprise one or more web browser extensions, add-ins, or add-ons. The toolbar may comprise one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™ PHP, Python™, and VB.NET, or combinations thereof.

In some cases, Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. The web browser, in some instances, is a mobile web browser. Mobile web browsers (also called mircrobrowsers, mini-browsers, and wireless browsers) may be designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Module

The medium, method, and system disclosed herein frequently comprise one or more softwares, servers, and database modules, or use of the same. In view of the disclosure provided herein, software modules may be created by techniques known to those of skill in the art using machines, software, and languages known to the art. The software modules disclosed herein may be implemented in a multitude of ways. In some cases, a software module comprises a file, a section of code, a programming feature, a programming structure, or combinations thereof. A software module may comprise a plurality of files, a plurality of sections of code, a plurality of programming features, a plurality of programming structures, or combinations thereof. By way of non-limiting examples, the one or more software modules comprise a web application, a mobile application, and/or a standalone application. Software modules may be in one computer program or application. Software modules may be in more than one computer program or application. Software modules may be hosted on one machine. Software modules may be hosted on more than one machine. Software modules may be hosted on cloud computing platforms. Software modules may be hosted on one or more machines in one location. Software modules may be hosted on one or more machines in more than one location.

Database

The medium, method, and system disclosed herein can comprise one or more databases, or use of the same. In view of the disclosure provided herein, those of skill in the art will recognize that many databases are suitable for storage and retrieval of geologic profile, operator activities, division of interest, and/or contact information of royalty owners. Suitable databases include, by way of non-limiting examples, relational databases, non-relational databases, feature oriented databases, feature databases, entity-relationship model databases, associative databases, and XML databases. In some cases, a database is internet-based. In some cases, a database is web-based. In some cases, a database is cloud computing-based. A database may be based on one or more local computer storage devices.

Data Transmission

The subject matter described herein, including methods for smell assessing of a subject, are configured to be performed in one or more facilities or at one or more locations. Facility locations are not limited by country and include any country or territory. In some instances, one or more steps are performed in a different country than another step of the method. In some cases, one or more method steps involving a computer system are performed in a different country than another step of the methods provided herein. In some cases, data processing and analyses are performed in a different country or location than one or more steps of the methods described herein. In some cases, one or more articles, products, or data are transferred from one or more of the facilities to one or more different facilities for analysis or further analysis. An article includes, but is not limited to, one or more panels used for testing. In some embodiments of the methods and systems described herein, the analysis is performed and a subsequent data transmission step will convey or transmit the results of the analysis.

In some cases, any step of any method described herein is performed by a software program or module on a computer. In additional or further embodiments, data from any step of any method described herein is transferred to and from facilities located within the same or different countries, including analysis performed in one facility in a particular location and the data shipped to another location or directly to an individual in the same or a different country. In additional or further embodiments, data from any step of any method described herein is transferred to and/or received from a facility located within the same or different countries, including analysis of a data input, performed in one facility in a particular location and corresponding data transmitted to another location, or directly to an individual, such as data related to the smell test, a diagnosis, a prognosis, or the like, in the same or different location or country.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "user" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

As used herein, the term "about" a number refers to that number plus or minus 15% of that number. The term "about" a range refers to that range minus 15% of its lowest value and plus 15% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The section headings used herein are for organizational purposes only and are not to be construed as limiting the subject matter described.

EXAMPLES

The following examples are included for illustrative purposes only and are not intended to limit the scope of the invention.

Example 1: A Rapid Test to Screen for Smell Loss

Smell tests can be costly and can be lengthy for population surveillance in health emergencies. To fill this gap, a smell test which evaluates smell in three ways in less than two minutes was developed. Its performance in discriminating between people with little or no sense of smell (anosmics) and individuals with other smell disorders from those with an average sense of smell (normosmics) was assessed. Also assessed was whether the smell test would perform similarly to the NIH Toolbox® Odor Identification Test in normosmics.

The smell test, described herein, measures olfaction by detection, intensity, and identification and the responses are collected via an online portal. Using Bayesian linear models, we compared the three outcome measures in adults with anosmia (N=111) and people with other smell disorders (e.g., hyposmia, parosmia, N=42) to people with no known problems in their sense of smell (N=154).

Participants

Eligible participants were recruited via a flyer distributed through the Monell Newsletter, allowing the enrollment of normosmic subscribers and subscribers with smell loss. Volunteers completed an eligibility survey in which they reported their age (inclusion criteria: 18-75 years old, 265 excluded), whether they had access to a smart device (phone or tablet) or a computer (6 excluded), and whether they were currently residing in the United States (121 excluded).

A total of 532 smell assessment tests were distributed by mail on a first-come, first-served basis; 308 participants reporting no history of smell problems received one smell assessment test, and one NIH Toolbox® Odor Identification Test. Participants with pre-existing forms of smell loss (N=224) received one smell assessment test, and were not asked to complete the NIH Toolbox® Odor Identification Test to limit the frustration generated by being confronted with smell tasks. Participants were also invited to take the smell assessment test (and the NIH Toolbox® Odor Identification Test, if available) on the same day they were scheduled to have a COVID-19 PCR test. Participants were then asked to report the results of the COVID PCR test via survey when the outcome was known. Only 3 participants took the smell test/s and the COVID PCR test, thus given the low numerosity this data is not shown. The response rate from completion of the eligibility survey was 79%, with a final sample size of participants who consented and completed the study including 154 normosmic adults, 111 anosmics and 42 participants with other smell disorders [fluctuations (N=5); hyposmia (N=23), parosmia (N=5), other (N=4), COVID-related smell loss (N=3)]. Given the low numerosity in each category of the smell disorders variable, no separate statistical analyses were performed on this factor. The normosmic participants who completed the NIH Toolbox® Odor Identification Test were 148.

Procedure

The study started on Sep. 4, 2020 and was completed by Sep. 15, 2020. During this time, participants were contacted via the Monell Newsletter, and completed an 10-question online eligibility survey. If they were not eligible or if they responded after the target number of participants had been enrolled, they were thanked and informed that they would not be enrolled in the study. If, on the contrary, they were deemed to be eligible, they received one or two smell tests via mail depending on their anosmic/normosmic self-report. Once participants received the test, they had to complete them within the next 14 days.

Participants used a QR-code or a web address to access the RedCap survey used to record self-reports on demographic data (age, gender, ethnicity), pre-existing smell and taste loss as well as complete the smell assessment test and the NIH Toolbox® Odor Identification Test, if available.

To complete smell test, the instructions were to (a) consecutively open one odor patch at a time, smell it and reseal it; (b) choose the strongest odor-containing patch from three patches, two of which do not have an odor; (c) rate on a scale from 0 to 100 the intensity of the odor detected; and (d) select the best verbal and visual label for the odor among four verbal and visual options. If the participant gave an incorrect response to (d), they were instructed to try again to identify the odor, this time among the three remaining options.

No feedback was provided on the accuracy of the odor identification after the second attempt. Intensity was included because a cutoff rating (e.g., <20 on a 1-100 scale) can be predetermined to signal smell loss for an odorant generally perceived as moderate to strong, and useful for tracking an individual's smell function over time (i.e., identifying changes with repeated testing). Additionally, it has been shown to be highly discriminative for COVID-19 infection.

The group of participants (normosmics) who also completed the NIH Toolbox® Odor Identification Test were instructed to scratch and sniff each of the 9 odors included in the NIH Toolbox® Odor Identification Test and identify among 4 visual and verbal options which one corresponded to the odor smelled. Participants identified a total of nine odors. Subsequently, the participants completing the NIH Toolbox® Odor Identification Test could opt in to answer questions regarding their health status, with particular reference to COVID-19 and other respiratory illnesses. Although no formal data were collected on the completion time of the smell assessment test, a limited number of participants (N=10) reported that the test takes ~2 minutes to complete when including the demographic questions and <1 minute to complete the smell test smell subtests.

Statistical Analysis

The cross sectional design includes a between-subject factor "Smell ability" (anosmic, other smell disorders, and normosmics) and within-subject factors, namely the scores at the subtests of smell test (odor discrimination, odor intensity, odor identification) as well as the smell assessment score (anosmia/normosmial), and the scores at the single items and the total score at the NIH Toolbox® Odor Identification Test.

Each smell test subtest returns one of the following scores: odor detection accuracy (correct/incorrect); odor intensity, (above/below a cut off of 20) and odor identification among 4 given options (correct/incorrect), and if the first response is incorrect, among the three remaining options (correct/incorrect). The NIH Toolbox® Odor Identification Test returns two scores: the official scoring (anosmia=<=3; hyposmia=4-6; normosmia >=7 (Dalton et al., 2013)) and a binarized version of the official score to directly compare the smell test score (anosmia=<=4; normosmia >=5).

A Sequential Bayes Factor design (SBFD) with maximal N was used. This may maximize the probability of obtaining the desired level of evidence and a low probability of obtaining misleading evidence. Additionally, this SBFD design may require on average half the sample size compared to the optimal null hypothesis testing fixed-n design, with comparable error rates. A desired grade of relative evidence for the alternative vs. the null (BF10) hypothesis was set at BF10>6 (moderate evidence) for H1 and BF01>3 for H0 (anecdotal evidence). Based on a conservative Cohen's D=0.5, a minimum sample size per group of n0=43 was specified. Once n0 was reached, the BF was computed on the existing data. BF computation continued after every participant was added (in the smallest or slowest accumulating group at that time) until the thresholds of H1 or H0 were reached, at which point sampling ceased. The main driver of the stop rule was, however, a time limit (September 15th). To test the hypotheses and explore the effect of covariates (age, sex, ethnicity), Bayesian linear mixed models using the BayesFactor package were used in the R Environment for Statistical Computing (R Core, 2020). Given the unequal distribution of the data across categories in the ethnicity variable, the responses were binarized as White/Non-white. To assess the differences in accuracy among tests and subtests, Bayesian and parametric tests were employed for equality of proportions with or without continuity correction.

Results

A small group of anosmics (N=11, 10%) successfully completed the smell assessment test. On the contrary, the majority of individuals with other smell disorders (N=27, 64%), as well as the vast majority of normosmics successfully completed the smell assessment test (N=145, 94%). Participants from the three groups differently used the response strategies to complete the smell assessment test. In the anosmic group, 23% of participants did not provide the correct response to any of the subtests, 41% did not successfully complete two subtests, and only 11% did not report an odor intensity above 20/100. In the other smell disorders group, 17% participants did not report an odor intensity above 20/100, 17% failed two out of the three subtests and only 2% did not provide the correct response to any of the subtests.

The combined accuracy at all three subtests may significantly discriminate the performance across the three groups. In particular, presently, the odor intensity score demonstrated a perfect ability to classify normosmia. In some cases, the only subtest that may not significantly discriminate between the performance of the three groups is the second odor identification, which was only used by a total of 32 participants across the three groups.

An identification test was used in order to compare the performance of the smell assessment test against a validated smell test. Results indicated that the performance at both tests was concordant when considering the odor identification of the flower odor, which was item #9 in the NIH Toolbox® Odor Identification Test (143/148, 97% participants correctly identified the flower odor) and the smell assessment odor identification subtest (136/148, 92% accuracy in the first identification attempt). A 2-sample test for equality of proportions with continuity correction confirmed a lack of statistical difference between the two test scores ($X2=2.25$, $df=1$, $p=0.13$). In 17/148 cases (12%) the NIH Toolbox® Odor Identification Test and the smell assessment test were discordant; in 12 cases the participant passed the NIH Toolbox® Odor Identification Test but failed the smell assessment test; in 5 cases the participant passed the smell assessment test but failed the NIH Toolbox® Odor Identification Test.

When considering the full NIH Toolbox® Odor Identification Test (9 items) and smell assessment test (detection, intensity and identification) the classification accuracy converged: 92% of normosmics passed both tests.

No effect of age (BF10=0.81±0.02%), sex (BF10=0.84±0.02%) or ethnicity (BF10=0.48±0.02%) was retrieved for the performance at the NIH Toolbox® Odor Identification Test.

Results from this study showed that smell tests described herein may be used as a quick, practical, and direct test to distinguish between people with and without smell loss. It may also distinguish smell disorders useful in many situations such as COVID-19 symptom screening. Clinical applications and population surveillance that smell assessment promotes are multiple, including the early detection of psychiatric, neurological and neurodegenerative disorders, such as schizophrenia, traumatic brain injury, Parkinson and Alzheimer's disease.

Example 2: Robust Description of a Smell Test—SCENTinel

Three components of olfactory function were combined to develop a rapid, accurate and inexpensive smell screening test. The test was developed with multiple odorants that have high familiarity in the US-population. Combining three objective measures made a fast, and accurate and inexpensive smell test.

There are validated measures to ascertain for smell ability (e.g., NIH Toolbox), but they are developed to determine the presence of smell disorders following quite involved procedures. To deploy a smell-based surveillance for COVID-19, a fast method would be useful, for instance, for screening for entry into the workplace or school, speed is important to prevent bottlenecks, and create groups of people. Currently, even the fastest available validated smell tests of the validated methods may be too time-consuming.

It may be important to include one or more components of olfactory function that can be objectively assessed so that we have a falsification metric and the ability to calculate the probability of passing the test in the absence of smell. The test includes 3 tasks:
  A detection task, in which only one out of three samples contain an odor, (e.g. pick the strongest odor-containing patch from three patches, two of which do not have an odor), which has a guessing probability of 33%
  Odor identification in which the individual needs to select the best label for the odor, (pick the most suitable picture/label for the odor out of a choice of 4)
  An intensity rating on a 0 to 100 scale with a cut-off rating (i., <20 on a 0-100 scale) to signal smell loss for an odorant that is generally perceived as moderate to strong.

The SCENTinel test comes in 8 different iso-intense fragrances, which allows for longitudinal within-subject testing for at least two working weeks, while providing enough variability to control for odor expectation as well as the rare possibility of specific anosmias. The fragrances allow for flexible use of the test across developmental stages, from children of 3 years old to the elderly, and from other smell identification tests standardized in the US population Given the fast nature of the test, a peel and smell sticker technology, which encapsulates the fragrance on a patch that delivers scent only when the top layer is lifted. This technology prevents cross-contamination across odor samples on the same card (useful for an accurate odor detection discrimination test) and allows the standardization of odor delivery across cards and odors (useful for an accurate odor intensity test), and limits the odor residual in the air post-test, which could greatly compromise the ability to identify the odors in an odor-saturated environment. Strategies like having a trained technician deliver the test (like in the NHANES case), represents an increased risk of contagion for person, and may not fully avoid that different test results may be confounded by different ways of scratching the odor patch. Relying on instructions provided to untrained participants may also not guarantee within and between participant administration standardization and as a consequence, the stability of the results may be affected. Pilot data collected with the peel and smell technology showed that the SCENTinel test takes most people less than two minutes to complete.

The components of the SCENTinel test are:
  A test backing material on which the odor labels and instructions are applied. The backing is card stock material or copy paper.
  3 odor labels, one with an odor, two blanks. The odors are scented oils. The labels are produced in rolls like address stickers which are then adhered to the backing.
  A software program to calculate the results. The user scans a QR code or enters a web site to complete an online survey. The survey asks a series of questions and the results are either returned to the user or added to a database. The survey in its current form is written in RedCap. REDCap is a secure web application for building and managing online surveys and databases. While REDCap can be used to collect virtually any type of data in any environment (including compliance with 21 CFR Part 11, FISMA, HIPAA, and GDPR), it is specifically geared to support online and offline data capture for research studies and operations.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A multifunctional smell assessment kit, comprising:
  a panel;
  a first surface adhered directly or indirectly to the panel by a first releasable adhesive, wherein the first releasable adhesive comprises an odorous volatile compound;
  a second surface adhered directly or indirectly to the panel by a second releasable adhesive not comprising any odorous volatile compound; and
  a system for registering whether the odorous volatile compound is detected by a user, comprising an input device that receives from the user:
    (a) a first input on whether the user detects, by olfaction, which of the adhesives comprises the odorous volatile compound,
    (b) a second input on whether the user identifies the odor of the volatile compound of (a), and
    (c) a third input comprising a rating on an intensity of the odorous volatile compound of (a) as perceived by the user,
    wherein input (a) is received first, followed by inputs (b) and (c) in any order.

2. The multifunctional smell assessment kit of claim 1, wherein the system further comprises a computer processor that, in connection with the input device, identifies the subject as having an olfactory impairment or as not having the olfactory impairment based on inputs (a), (b), and (c).

3. The multifunctional smell assessment kit of claim 1, wherein the first surface or the second surface comprises plastic, rubber, silicone, or paper.

4. The multifunctional smell assessment kit of claim 1, wherein the first or second releasable adhesive comprises a glue, a resin, a rubber adhesive, or an acrylic adhesive.

5. The multifunctional smell assessment kit of claim 1, further comprising a third surface adhered directly or indirectly to the panel by a third releasable adhesive not comprising any odorous volatile compound, and wherein the multifunctional smell assessment kit comprises no more than three surfaces adhered directly or indirectly to the panel by releasable adhesives.

6. The multifunctional smell assessment kit of claim 1, wherein the panel comprises paper, card stock, plastic, rubber, metal, or silicone.

7. The multifunctional smell assessment kit of claim 1, wherein the first releasable adhesive temporarily adheres the first surface directly or indirectly to the panel while retaining the odorous volatile compound.

8. The multifunctional smell assessment kit of claim 1, wherein the panel comprises a printed symbol or code indicating the odor, or indicating that the first releasable adhesive comprises the odorous volatile compound.

9. The multifunctional smell assessment kit of claim 1, wherein the panel is indirectly adhered to the first and second surfaces, the first releasable adhesive is directly adhered to a third surface directly adhered to the panel, and the second releasable adhesive is directly adhered to a fourth surface directly adhered to the panel.

10. The multifunctional smell assessment kit of claim 1, wherein the system further comprises an output device that displays a scale, and the third input comprises a selection made by the user of a position on the scale.

11. A smell assessment method, comprising:
identifying a subject suspected of having an olfactory impairment;
administering to the subject a panel comprising a first peelable surface adhered directly or indirectly to the panel by a first adhesive, wherein the first adhesive comprises an odorous volatile compound detectible by a person of ordinary olfactory ability, wherein the panel comprises a second peelable surface adhered directly or indirectly to the panel by a second adhesive not comprising any odorous volatile compound;
obtaining from the subject:
(a) whether the subject detects, by olfaction, which of the adhesives comprises the odorous volatile compound,
(b) whether the subject identifies an odor of the volatile compound of (a), and
(c) a rating of an intensity of the odorous volatile compound of (a) as perceived by the subject; and
identifying the subject as having the olfactory impairment or as not having the olfactory impairment based on (a), (b), and (c).

12. The smell assessment method of claim 11, wherein (a) comprises a determination of which of the first peelable surface and the second peelable surface the subject considers to comprise a stronger odor.

13. The smell assessment method of claim 11, wherein (b) comprises a determination of which of a first image or a second image comprises an image corresponding to the odor, wherein the first image comprises an image corresponding to the odor, and wherein the second image comprises an image not corresponding to the odor.

14. The smell assessment method of claim 11, wherein the rating comprises a quantitation of the intensity of the odorous volatile compound of (a) as perceived by the subject.

15. The smell assessment method of claim 11, wherein the identifying the subject as having the olfactory impairment or as not having the olfactory impairment is performed by a computer system.

16. The smell assessment method of claim 15, further comprising: identifying the subject as likely to have a disease or disorder when the subject is identified as having the olfactory impairment, and identifying the subject as unlikely to have the disease or disorder when the subject is identified as not having the olfactory impairment.

17. The smell assessment method of claim 16, wherein the disease or disorder comprises coronavirus disease 2019 (COVID-19).

18. The smell assessment method of claim 17, further comprising administering to the subject a COVID-19 treatment.

19. The smell assessment method of claim 16, wherein the disease or disorder comprises a traumatic brain injury, Parkinson's disease or Alzheimer's disease.

20. The smell assessment method of claim 19, further comprising administering to the subject a traumatic brain injury treatment, a Parkinson's disease treatment or an Alzheimer's disease treatment.

* * * * *